United States Patent
Forstner

(10) Patent No.: US 10,390,753 B2
(45) Date of Patent: Aug. 27, 2019

(54) BLISTER STRIP

(71) Applicant: Bernhard Forstner, Linz (AT)

(72) Inventor: Bernhard Forstner, Linz (AT)

(73) Assignee: ALLTEST GmbH, Linz (AT)

(*) Notice: Subject to any disclaimer, the term of this patent is extended or adjusted under 35 U.S.C. 154(b) by 115 days.

(21) Appl. No.: 15/520,988

(22) PCT Filed: Oct. 16, 2015

(86) PCT No.: PCT/AT2015/050258
§ 371 (c)(1),
(2) Date: Apr. 21, 2017

(87) PCT Pub. No.: WO2016/061600
PCT Pub. Date: Apr. 28, 2016

(65) Prior Publication Data
US 2017/0340263 A1 Nov. 30, 2017

(30) Foreign Application Priority Data
Oct. 21, 2014 (AT) .................................. 50755/2014

(51) Int. Cl.
A61B 5/00 (2006.01)
A61B 10/00 (2006.01)
(Continued)

(52) U.S. Cl.
CPC .......... A61B 5/411 (2013.01); A61B 10/0035 (2013.01); A61B 17/205 (2013.01);
(Continued)

(58) Field of Classification Search
CPC combination set(s) only.
See application file for complete search history.

(56) References Cited

U.S. PATENT DOCUMENTS 2,841,138 A * 7/1958 Laub .................... A61B 17/205
600/556
4,205,689 A * 6/1980 Brennan ................ A61B 10/00
206/439
(Continued)

FOREIGN PATENT DOCUMENTS

EP 0734964 10/1996
JP 19820217893 8/1983
(Continued)

OTHER PUBLICATIONS

International Search Report for PCT/AT2015/050258, English translation attached to original, Both completed by the European Patent Office dated Feb. 1, 2016, All together 7 Pages.
(Continued)

Primary Examiner — Eric J Messersmith
(74) Attorney, Agent, or Firm — Brian E. Hennessey

(57) ABSTRACT

A blister strip which can be stuck onto the skin, is formed from at least two sheets and has an applicator for applying a medium contained in the blister to the skin, wherein the blister strip includes an upper sheet, with at least one protuberance, wherein the underside of the upper sheet, the underside enclosing the protuberance, is of adhesive configuration. The blister strip has a lower sheet, which covers the lower surface of the blister strip and can be drawn off from the adhesive underside of the upper sheet. The protuberance contains an applicator, separating the protuberance into at least two sub-volumes. Wherein the applicator has at least one opening, which connects two sub-volumes, wherein one sub-volume is located between the applicator and the lower sheet, and wherein at least one sub-volume is entirely surrounded by the inner surface of the protuberance and the applicator, and contains the medium.

21 Claims, 4 Drawing Sheets

Figure 1:
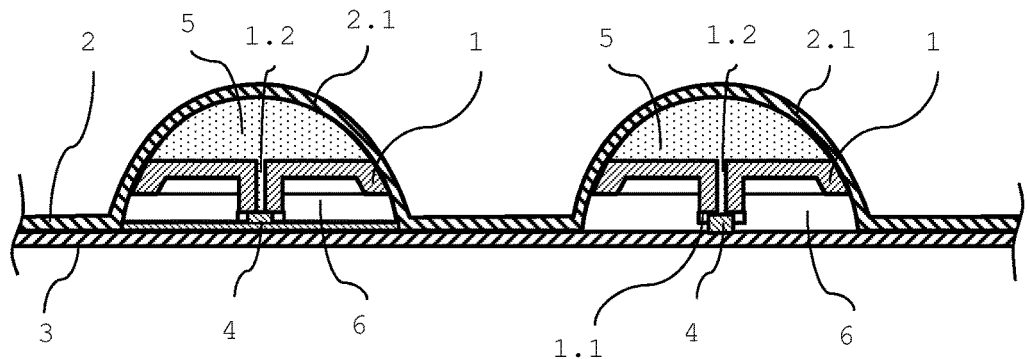

(51) Int. Cl.
    *A61B 17/20*     (2006.01)
    *A61M 5/19*     (2006.01)
    *A61M 5/28*     (2006.01)
    *A61M 5/32*     (2006.01)

(52) U.S. Cl.
    CPC .............. *A61M 5/19* (2013.01); *A61M 5/282* (2013.01); *A61M 5/32* (2013.01); *A61M 5/3298* (2013.01)

(56) References Cited

U.S. PATENT DOCUMENTS

| | | | |
|---|---|---|---|
| 4,237,906 A * | 12/1980 | Havstad | A61B 17/205 |
| | | | 215/250 |
| 4,473,038 A | 9/1984 | Maganias | |
| 4,802,493 A * | 2/1989 | Maganias | A61B 17/205 |
| | | | 600/556 |
| 4,966,159 A | 10/1990 | Maganias | |
| 5,099,857 A * | 3/1992 | Baldo | A61B 5/411 |
| | | | 600/556 |
| 5,104,620 A | 4/1992 | Wiley et al. | |
| 5,179,959 A | 1/1993 | Fishman et al. | |
| 2006/0167375 A1 | 7/2006 | Terrasse et al. | |
| 2007/0276284 A1 | 11/2007 | Utsugi | |
| 2014/0276196 A1 | 9/2014 | Niederauer et al. | |
| 2015/0126898 A1 * | 5/2015 | Sullivan | A61B 5/411 |
| | | | 600/556 |

FOREIGN PATENT DOCUMENTS

| | | |
|---|---|---|
| JP | 2005087520 | 4/2005 |
| KR | 101018406 | 2/2011 |
| WO | 8705200 | 9/1987 |
| WO | 8809149 | 12/1988 |
| WO | 9632142 | 10/1996 |

OTHER PUBLICATIONS

Notice of Reasons for Refusal, JP Application No. 2017-522426, dated Apr. 2, 2019.

Search Report, JP Application No. 2017-522426, dated Mar. 20, 2019.

* cited by examiner

BLISTER STRIP

CROSS-REFERENCE TO RELATED APPLICATION

This application is the U.S. national phase of PCT Application No. PCT/AT2015/050258 filed on Oct. 16, 2015, which claims priority to AT Patent Application No. A50755/2014 filed on Oct. 21, 2014, the disclosures of which are incorporated in their entirety by reference herein.

The invention relates to a blister strip for sticking onto the skin, in particular for carrying out an allergy test.

A blister strip is a laminar structure which comprises at least two layers, wherein one or more cavities are located between the layers, the cavities being referred to as blisters. Blister strips are known, for example, as drug packaging, wherein active substances are contained in the blisters in the form of pills which can be pressed out of the blister. A blister strip here consists of two films, wherein the lower film is flat and the upper film has dome-shaped, dimensionally stable protuberances (bulges, blisters), and therefore cavities are formed between the films. By application of pressure onto the dome of the upper film, the lower film is torn off and the contents of the cavity emerge.

In order to carry out an allergy test, test strips are known which can be applied to the skin and contain an allergen in a capsule or a cavity, said allergen generally being present in a liquid or gel-like carrier substance. In these allergy tests, the allergen can be brought into contact with the skin by opening or destroying the capsule or cavity. It is known according to the prior art to design said allergy test strips as blister strips. According to the prior art, blister strips are also known which can be stuck onto the skin of the person to be tested.

In the case of the blister strips which can be stuck on and contain liquid allergens, it is known to produce said blister strips in accordance with the above-described drug packaging design. During use, the lower film is stuck onto the skin. An applicator is attached to the inner side of the dome of the upper film, said applicator being capable of piercing the lower film and optionally also of slightly penetrating the skin. The dome is at least partially filled with liquid, wherein the latter emerges through the hole in the film and is thus intended to pass onto or into the skin. Blister strips according to this principle are shown, for example, in WO 8705200 A1 and US 2014276196 A1. A disadvantage of this design is that the film has to pierced with the applicator, which may have the consequence of an irregular or unreliable discharge of the allergen, or entails the risk of parts of the film penetrating the skin. It is disadvantageous that this design permits only a virtually punctiform introduction of the allergen, and the liquid may pass between skin and film, with the risk of mixing.

In the case of other blister strips which can be stuck on, it is known to provide the allergen as a gel, or to keep the allergen in liquid in an absorbent substrate, or to keep the liquid on the inner side of the blister by means of surface tension. Blister strips with this principle are shown, for example, in U.S. Pat. Nos. 4,802,493A, 4,966,159A and US2007276284A1. In this case, the lower film can be removed prior to the application of the blister strip, without liquid emerging. An applicator can again be present on the inner side of the dome of the upper film, with which applicator the skin can be injured to a small extent. It is disadvantageous that the allergen has to be present in an absorbent substrate or as a gel, and there is also the risk that, during handling after the film has been pulled off, the allergen is applied at a wrong location or the gel or the absorbent substrate is contaminated with other allergens (for example from other blisters).

U.S. Pat. No. 5,099,857 A furthermore indicates providing an additional capsule in the blister below the applicator, said capsule being destroyed in order to release the test liquid.

The object on which the invention is based consists in providing a blister strip for allergy tests, which blister strip can be stuck on, has a simple design and permits the use of liquid test substances, wherein an applicator is intended to be attached in the blister, said applicator permitting a controlled slight injury of the skin, wherein the intention is for no film to be pierced during the use of the applicator.

To achieve the object, it is proposed to design the applicator and to arrange the same in the blister in such a manner that said applicator separates the blister into two regions. The first region lies between the inner side of the preferably dome-shaped protuberance of the upper film and the applicator and is consequently referred to as a liquid reservoir. The second region lies between the applicator and the lower film and is consequently referred to as the squeezing-out reservoir. By means of the applicator, the two regions are separated from each other in a sealed manner in the unopened state of the blister strip.

In order to apply the blister strip, the lower film is pulled off from the strip, thus exposing the lower side of the upper film, which is provided with a skin-compatible adhesive at least in the region around each blister. The lower side of the upper film is now stuck onto the skin, and therefore the squeezing-out reservoir is now formed by the applicator, optionally by the side walls of the protuberance below the applicator, and the skin. By exertion of a force on the dome of the blister, the liquid of the liquid reservoir is moved through an opening in the applicator into the squeezing-out reservoir.

If, after the liquid reservoir is squeezed out, the force on the applicator is increased somewhat further, said applicator is moved in the direction of the skin, and, for example, by finger pressure and careful circulating massaging movement of the applicator, the skin can be superficially injured in the form of scratches and the allergen liquid can penetrate into the uppermost skin layers.

The action of force is subsequently removed and the blister strip is left for some minutes on the skin in order to wait for a reaction of the body to the allergen before the blister strip is pulled off.

The invention is illustrated with reference to drawings:

FIG. 1: shows, in a sectional view, the design of an exemplary blister strip according to the invention.

Figure 2:
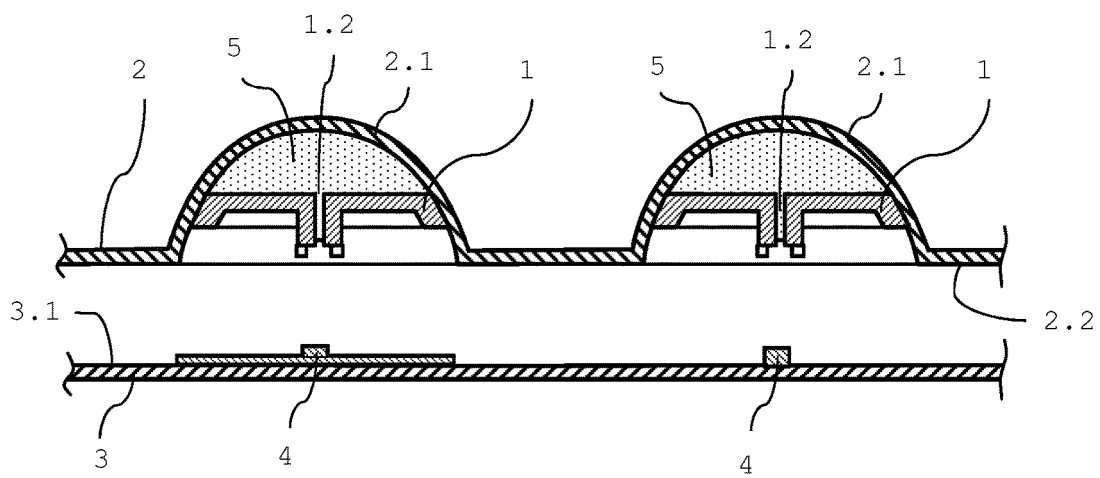

FIG. 2: shows, in a sectional view, an exemplary blister strip according to the invention after removal of the lower film.

Figure 3:
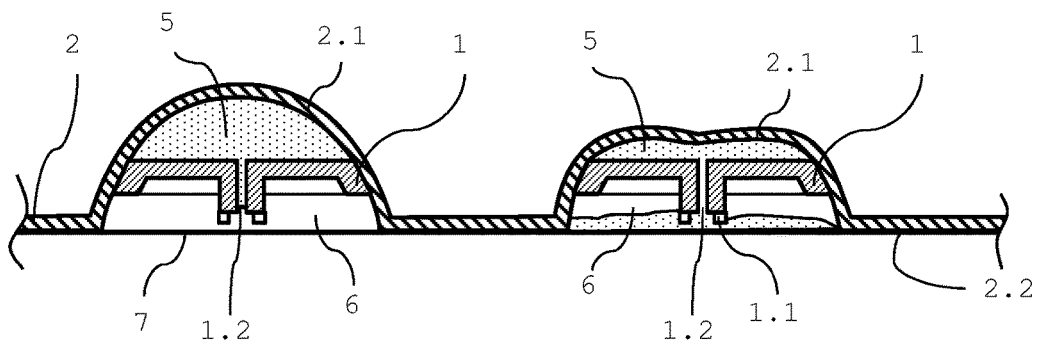

FIG. 3: shows, in a sectional view, an exemplary blister strip according to the invention which is stuck onto the skin, with a blister applicator in the starting state and with an applicator which has already been pressed in and in which the allergen liquid has thus been squeezed out into the squeezing-out reservoir.

Figure 4:
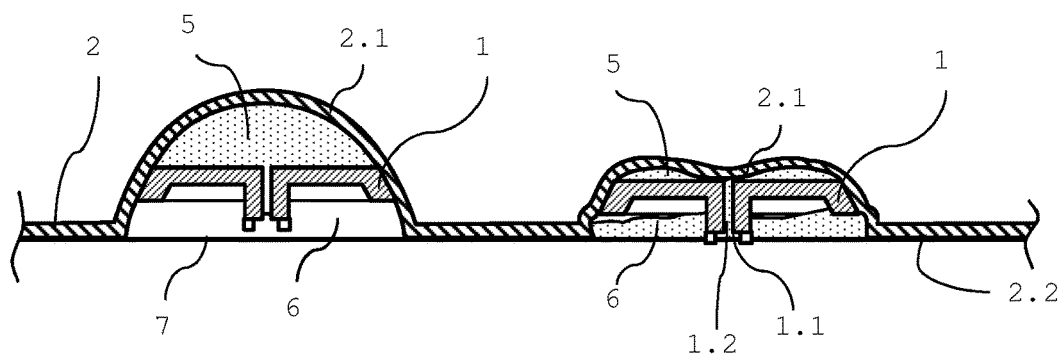

FIG. 4: shows, in a sectional view, an exemplary blister strip according to the invention which is stuck onto the skin, with a pressure-actuated applicator and skin penetration which has taken place.

Figure 5:
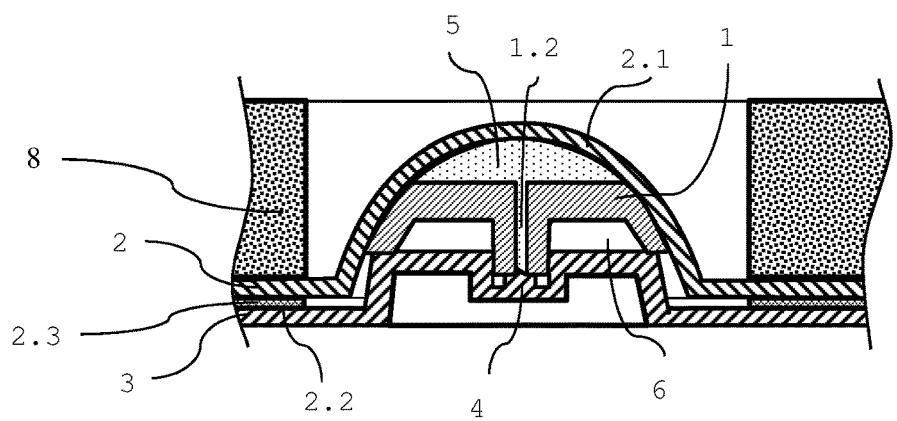

FIG. 5: shows, in a sectional view, an exemplary blister strip according to the invention with alternative configurations.

Figure 6:
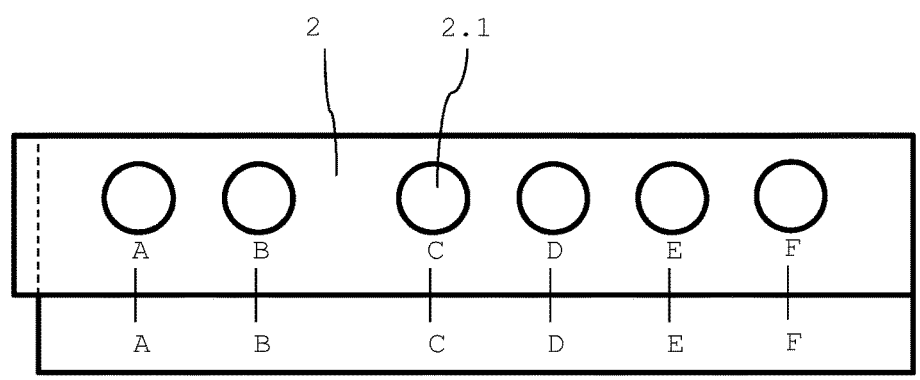

FIG. 6: shows an exemplary blister strip according to the invention from above.

FIG. 7: FIGS. 7*a* to 7*d* show, in a sectional view, an exemplary blister strip according to the invention in a plurality of steps of an exemplary production process.

Figure 8A:
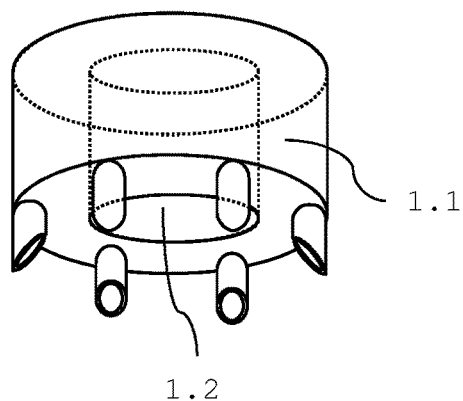
Figure 8B:
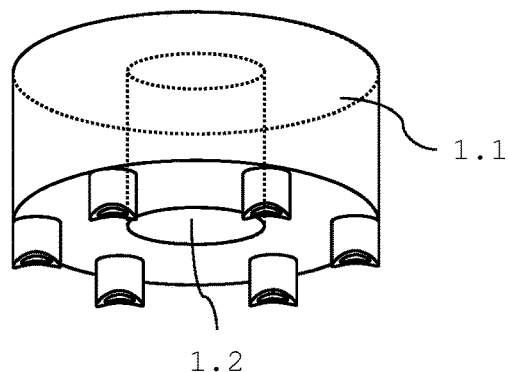
Figure 8C:
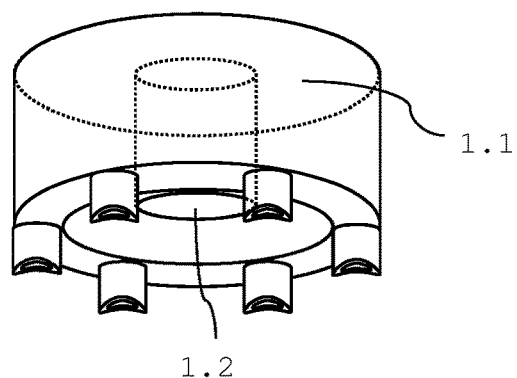

FIG. 8: FIGS. 8*a* to 8*c* show exemplary applicator points according to the invention.

Insofar as the direction indications at the top and at the bottom or upper and lower are used in the description of the figures, this refers to the position of the blister strip in alignment with the surface to which the strip is applied as intended during the application. At the bottom or the lower side is therefore the side which lies facing said surface.

FIG. 1 shows the design of a preferred blister strip according to the invention, wherein two blisters are shown in cross section, wherein each blister is formed by a protuberance 2.1 of the upper film 2, which, as is illustrated, preferably has a dome shape. An applicator 1 is attached inside each blister and is adhesively bonded on the annular contact surface to the inner side of the protuberance 2.1, or is compressed with said inner side in a liquid-tight manner. The protuberance 2.1 is thus divided into two regions by the applicator 1. The applicator 1 has an opening 1.2 through which liquid can pass during the application of the blister strip.

The two regions are separated from each other in a sealed manner in the unopened state of the blister strip, which can be achieved, for example, by a sealing stopper 4 which is connected by adhesive bonding to the lower film 3 and can thus be removed with the latter. This sealing stopper 4 can close, for example, only the opening 1.2, or, as illustrated in the left blister, the entire area of the blister. This embodiment has the advantage that the sealing stopper 4 can easily be inserted mechanically and, during the manufacturing of the blister strip, no adhesive can pass into the blister or onto the applicator point 1.1.

The applicator 1 preferably has a disc shape, wherein the edge of the disc is somewhat wider and projects downward from the disc in order to increase the contact surface with the protuberance 2.1.

The applicator point 1.1 likewise protrudes downward centrally from the applicator 1, wherein the applicator point 1.1 preferably protrudes further downward than the edge of the disc, and therefore, when the applicator 1 is pressed downward, said applicator point comes into contact with the skin before the edge of the disc; otherwise, the applicator 1 itself would have to be somewhat deformable, preferably elastically deformable, such that its center and therefore the applicator point 1.1 could be moved somewhat downward when the edge of the disc is already in contact with the skin 7. The disc is preferably inserted in such a manner that, below the disc, the dome walls of the protuberance 2.1 form a boundary of the squeezing-out reservoir 6, i.e. the lower end of the edge of the disc is inserted into the protuberance 2.1 spaced apart from the lower side 2.2 of the film 2. If the protuberance 2.1 has a dome shape, the surface with which the disc lies against the protuberance 2.1 is preferably matched to the shape of the dome, i.e. is designed to be annular and in a manner tapering upward, and therefore the disc is approximately a conical disc or spherical disc.

The applicator point 1.1 is that part of the applicator 1 which can be brought into contact with the skin 7 in order to be able to cause a slight lesion of the latter. The applicator point 1.1 here has one or more sharp or pointed elements or edges with which the skin 7 can be scratched or scored or penetrated in a punctiform manner. The applicator point 1.1 here can be a hollow needle point or pricking needle point or can have a plurality of said points, or, similarly to sandpaper, can have a plurality of geometries projecting regularly or irregularly from the surface. The sharp or pointed elements are preferably attached annularly around the opening 1.2 of the applicator 1, the opening preferably running centrally in the applicator point 1.1. If the applicator point 1.1 is a hollow needle, the opening of the hollow needle can be the opening 1.2 of the applicator 1.

Three exemplary, particularly preferred applicator points 1.1 according to the invention are shown in FIGS. 8*a*, 8*b*, 8*c*. The applicator point according to the invention has been invented specifically for this application, but, because of the advantageous configuration, said applicator point can also be used for other applications, for example for the advantageous improvement of known (allergy test) applicators. The applicator point 1.1 according to the invention has at least one preferably central opening 1.2, and is designed, for example, as a cylinder. On the side facing the skin 7 or the lower film 3, the applicator point 1.1 has a plurality of sharp or pointed elements which are preferably arranged annularly around the opening 1.2. Said elements are particularly advantageously formed by hollow needle points which can receive a small quantity of liquid during the application and can introduce said liquid into the skin 7, or, after penetration of the uppermost skin layers, can introduce it in a delayed manner by contact with the allergen liquid. As shown in FIG. 8*a*, conventional, obliquely trimmed hollow needles can be used as the pointed elements, wherein said hollow needles can penetrate into the skin to the extent that they protrude out of the applicator point 1.1.

Preferably, the hollow or penetrator needles are not offset obliquely, but rather horizontally, as shown in FIGS. 8*b* and 8*c*, in order to avoid deep penetration and therefore actually only to penetrate the uppermost skin layer. The shape of the penetrator needle point here is particularly preferably formed concavely, in the shape of a trough, and can also be provided with a very fine toothing on the periphery.

As shown in FIG. 8*c*, the applicator point 1.1 itself can preferably be formed in a trough-shaped or concave manner on the lower side, and therefore a greater quantity of liquid can remain in the region between the pointed or sharp elements. This can be achieved, for example, by the fact that the small opening 1.2 at the lower end has a phase, rounded portion or depression in order to increase the diameter thereof. The applicator point 1.1 is preferably manufactured by injection molding, wherein preferably also the pointed or sharp elements and/or the applicator 1 are formed in the injection mold, and therefore an applicator 1 which is finished ready for use is manufactured in one working step. If the pointed or sharp elements are composed of a different material than the applicator point 1.1, said elements are preferably inserted into the injection mold such that they can be partially embedded into the material of the applicator point during the injection molding. As illustrated in FIG. 2, the lower film 3 can be pulled off, wherein the upper surface 3.1 of the lower film 3, which surface lies against the lower side 2.2 of the upper film 2, is designed as an adhesive protective film. So that the sealing stopper 4 adhere to the lower film 3, it is possible for the lower film 3 not to be designed as an adhesive protective film in the region of the sealing stopper 4. By pulling off the lower film 3 with the sealing stopper 4, the adhesive lower side 2.2 of the upper film 2 and the opening 1.2 of the applicator 1 are exposed. The liquid does not pass through the opening 1.2, as long as no pressure is exerted on the protuberance 2.1, since no air can penetrate into the liquid reservoir 5 through the small opening 1.2.

The sealing stopper 4 therefore serves, during the storage or handling of the unopened blister strip, to prevent the liquid reservoir 5 from being emptied into the squeezing-out reservoir 6 by unintentional compression of the protuberance 2.1.

As illustrated in FIG. 3, the opened blister strip is stuck with the adhesive lower side 2.2 of the upper film 2 onto the skin 7, as a result of which a cavity which is sealed off from the surroundings is formed between applicator 1 and the skin 6 in the form of the squeezing-out reservoir 6. As can be seen in the second blister of FIG. 3, by compression of the protuberance 2.1 the volume of the liquid reservoir 5 can be reduced, as a result of which the liquid is pressed through the opening 1.2 of the applicator 1 and passes into the squeezing-out reservoir 6.

As illustrated in the second blister in FIG. 4, by further compression of the protuberance 2.1, the applicator 1 can be brought into contact with the skin 7. This takes place if the inner side of the protuberance 2.1 lies against the applicator 1, or if the resistance of the liquid to squeezing out is higher than the resistance of the dome side walls, which laterally bound the squeezing-out reservoir 6 below the applicator 1, to deformation.

Owing to the dome geometry, the compression of the upper flat dome cap which bounds the liquid reservoir 5 requires less force than the compression of the steep dome side walls below the applicator 1.

If the applicator point 1.1 is in contact with the skin 7, the allergen can be introduced into the skin 7 by slightly circling massaging of the blister. For this purpose, the sharp or pointed elements of the applicator point 1.1 penetrate somewhat into the skin 7. By suitable configuration of the applicator point 1.1, for example by the distance with which the sharp or pointed elements protrude out of the applicator point 1.1, it can be determined how deep or into which skin layer the allergens penetrate. The present design is also advantageous if the applicator 1 does not have any pointed or sharp elements, for example for carrying out epicutaneous tests.

Depending on the size of the blister or depending on the quantity of liquid in the liquid reservoir 5, it may be necessary to provide an option in order to allow the air enclosed in the squeezing-out reservoir 6 to escape so that said air is not pressed under the adhesive layer of the film 2 with an inadvertent and uncontrolled escape of liquid possibly taking place as a result. One option is to provide a predetermined breaking point so that liquid can only escape laterally under the adhesive layer and therefore passes into the surroundings and not into another blister. A further option would be to connect the squeezing-out reservoir 6 to an expandable volume, for example to a second, empty, compressed blister, or to a further, separated volume which lies between the protuberance 2.1 and the applicator 1 and is compressed in the starting state.

If the blister has a very small surface in comparison to the adhesive surface (or the distance between two blisters is sufficiently large), or the volume of the liquid reservoir 5 is small in comparison to the volume of the squeezing-out reservoir 6, the provision of an air outlet can be omitted.

The volume of the liquid reservoir 5 is preferably circa one fifth of the volume of the squeezing-out reservoir 6. The volume of the liquid reservoir 5 is preferably between 20 and 30 µl. In this case, the provision of an air outlet is not necessary since the small change in volume of the squeezing-out reservoir 6 by introduction of the liquid is compensated for by the elastic flexibility of the skin 7. During the application, by moving the point 1.1 onto the skin 8, the volume of the squeezing-out reservoir 6 is also somewhat reduced, or the small positive pressure in the squeezing-out reservoir 6 is somewhat increased, which leads to a further curvature of the skin 7. Since the allergy test is customarily carried out on the forearm or on the back of the horizontal patient, a small trough in which the liquid collects thus arises in the skin 7 in the center of the blister.

As an option for compensating for the additional volume from the liquid reservoir 5 or for the volume of the squeezing-out reservoir 6, which is reduced by pressing down the applicator 1, the adhesive application on the lower side 2.2 of the upper film 2 can take place somewhat spaced apart from the blister, as shown in FIG. 5. In this case, the adhesive application is formed by a double-sided adhesive film 2.3. As illustrated in FIG. 5, the blister strip can have an additional protective layer 8 which rests on or is fastened to the upper surface of the upper film 2. Said protective layer 8 which is preferably formed from cardboard or foamed plastic has recesses for the blisters and protects the blisters from damage during storage or while being stuck onto the skin 7. The application is not obstructed by the protective layer 8 since the blister is accessible through the opening in the protective layer 8. It is also shown in FIG. 5 that the lower film 3 can also be thermoformed in the region of the blister, and therefore said film itself forms the sealing stopper 4 or closes the opening 1.2 and/or the entire area of the blister.

A dimensionally stable material, such as hard plastic, in particular transparent hard plastic, is suitable as material for the applicator 1. The applicator 1 is particularly preferably manufactured cost-effectively by injection molding. The sharp or pointed elements of the applicator point 1.1 can likewise be composed of hard plastic and connected monolithically to the applicator 1. The sharp or pointed elements can also be composed of metal, glass or another hard, sharp-edged material.

The upper film 2 or lower film 3 can be a plastics film or aluminum foil (in particular hard aluminum foil), or a laminate, i.e. a laminar structure consisting of a plurality of films. The upper film 2 or the protuberance 2.1 can preferably be formed transparently. The upper film 2 or the material of the protuberance 2.1 is plastically deformable here such that, after removal of the compressive force from the protuberance 2.1, the latter remains in the deformed state. In the case of an elastic protuberance 2.1, after removal of the force, the latter would return again into its starting shape and would thus partially suck the liquid back from the squeezing-out reservoir 6 into the liquid reservoir 5, which would possibly even be desirable for some applications. In the case of the side walls of the protuberance 2.1, which are located below the applicator 1, an elastic deformation back may be desirable so that, after the application has taken place, the applicator point 1.1 is moved away somewhat from the skin 7 and therefore the sharp or pointed elements are not in contact with the skin 7 throughout the entire test time. The same can be achieved in the case of plastically deformable side walls if, after the application, by pulling on the applicator 1 the latter is moved away somewhat from the skin 7.

The production of a blister strip, as illustrated in FIGS. 7*a*-7*d*, can take place in the following steps:

Stamping (or thermoforming, etc.) the upper film 2, as a result of which the latter is permanently deformed in order to form the blisters.

Figure 7A:
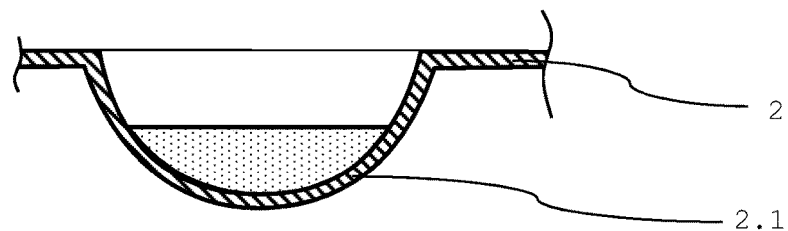

As shown in FIG. 7*a*, the liquid is passed into the blister, the upper film 2 here faces with the lower side upward, and therefore the blister forms a trough.

Figure 7B:
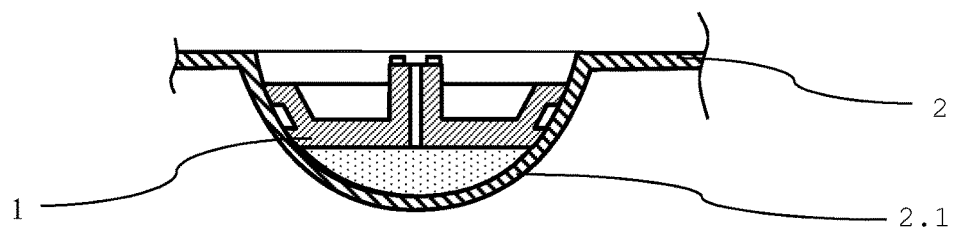

As shown in FIG. 7b, the applicator 1 is inserted into the blisters.

Figure 7C:
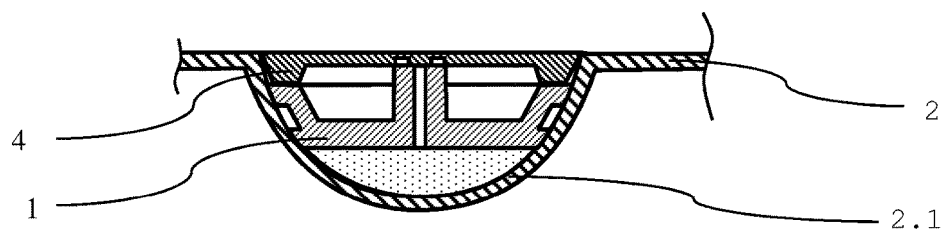

As shown in FIG. 7c, the opening 2.1 or the blister is closed with the sealing stopper 4. Alternatively, the applicator 1 and the sealing stopper 4 can be jointly inserted.

Figure 7D:
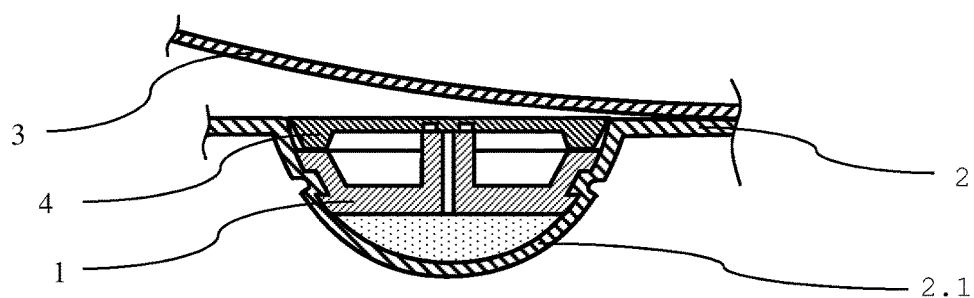

As shown in FIG. 7d, the blister strip is provided with the lower film 3 which covers the sealing stopper 4 and the upper film 2.

As furthermore shown in FIG. 7d, the upper film 2 is connected to the annular lateral surface of the applicator 1.1, for example by said film being pressed against the applicator 1, for which purpose, as illustrated, the lateral surface of the applicator 1 can have a groove or another surface structure (for example a plurality of indentations or a plurality of vertically and/or horizontally running grooves) such that the upper film 2 is connected in a form-fitting manner to the applicator 1 (without adhesive bonding or welding). Alternatively, the upper film 2 can be welded to the applicator 1 by brief action of heat and pressure. The upper film 2 can be connected to the applicator 1 at any time after insertion of the applicator 1.

In order to releasably adhesively bond the lower film 3 to the upper film 2, the upper film 2 can already be provided with an adhesive layer prior to the introduction of the liquid, or, for example, only after the sealing stopper 4 has been inserted. The sealing stopper 4 can likewise already have an adhesive layer or at least one punctiform adhesive application before the insertion, or else can be provided therewith after the insertion. The adhesive layer of the sealing stopper 4 preferably has a different composition than the adhesive layer of the upper film 2, and therefore the adhesive layer of the sealing stopper 4 strongly adheres to the adhesive protective layer of the lower film 3. Alternatively, the adhesive layer can be applied together with the lower film 3 by the latter being connected in the region of the lower side 2.2 of the upper film 2 to the adhesive layer in a slightly adhesive and therefore releasable manner. In the region of the sealing stopper 4, the lower film 2 adheres strongly and is therefore connected non-releasably to an adhesive layer.

The provision of the lower side 2.2 of the film 2 and of the lower side of the stopper 4 with adhesive takes place, for example, by coating or sticking on a double-sided adhesive film. The double-sided adhesive film here is highly adhesive in the direction of the upper film 2, is skin-compatible in the direction of the skin and is adhesive to an extent such that the test can be carried out without causing a great amount of pain as the adhesive film is being pulled off.

Alternatively to the described method, the liquid can be injected through the opening 1.2 of the applicator 1 after said applicator has been inserted into the blister and adhesively bonded to the blister. The applicator in this case preferably has at least two opening 1.2, and therefore air can escape through the second opening during the filling.

After application of the lower film 3, the blisters and the applicators 1 arranged therein are packaged in a sterile manner and protected against contamination. An advantage of the present design of the blister strip is that the latter is to be opened only immediately prior to application and an additional instrument does not have to be used. The allergy test strip is therefore storable and transportable and can be used by untrained staff and even in hygienically dubious ambient conditions without there being an increased risk of infection for the person being investigated or for the applier.

Since, owing to the simple design, the allergy test strip can be produced in an advantageous manner in mass production and is extremely simple and safe to apply, it is excellently suited for rapid allergy tests with little expenditure of time for professionals or for self-application.

The blister strip has at least one allergen-containing blister. In addition, a blister can be present which contains the liquid without an allergen, in order to carry out the negative control, and/or a blister with histamine in order to carry out the positive control.

In addition, any desired number of further blisters can be present, wherein each contains an allergen to be tested. The blister strip can have one row of blisters, or two or more parallel rows of blisters. The blister strip preferably has a row with 8 blisters. For example, a person can thus be tested for 14 allergens (including a positive and a negative test) with two differently loaded blister strips, with application of one strip each on the inner side of each forearm. The loading of the blister strips can be adapted to the respective area of use (for example geographically, or investigation of individual allergen groups, for example animals/trees/grasses . . . ).

The blister strip can be combined with an adhesive strip which, after the blister strip is pulled off, remains on the skin and bears the respective identification of the substance contained in the blister, as shown in FIG. 6. The identification can also be attached to the blister strip itself and transferred, for example, manually. A further allocation possibility would be to arrange two or more blisters at a characteristic distance from one another so that, from the position of the, for example, increased distance, the position of the blister strip on the skin after being pulled off can be reconstructed, or a template can be applied only in one way and therefore unambiguously. A further possibility would be to arrange one more blisters offset from the other blisters arranged in a row.

Reference will also be made by way of example and in no way definitively to the following possible generalizations in relation to the preferred configuration of the invention depicted in the description of the figures, which generalizations are intended according to the invention to be covered by the present scope of protection.

The blister or the protrusion of the upper film can have a shape differing from the dome, for example can be cylindrical or rectangular, or can have a complex volume which consists, for example, of a cavity with two or more domes.

Instead of the sealing stopper 4 or in addition, the applicator 1 can have a thin membrane which closes the opening 1.2 and tears when pressure is exerted.

It is also conceivable for the applicator to separate the blister into three or more partial regions which are sealed in relation to one another, and a connection is opened only during the application. For example, the allergen or an active substance can thus be present as a solid in one partial region and can be dissolved in the liquid from another partial region only directly during the application. The medium contained in the first partial region, i.e. in the liquid reservoir 5, can be, in addition to liquid, also a gel, grease or Vaseline.

The invention claimed is:

1. A blister strip which can be stuck onto skin and is formed from at least two films and comprises at least one applicator for applying a medium contained in a blister and the substances contained in the medium onto or into the skin, wherein the blister strip comprises an upper film which has at least one protuberance, wherein the lower side of the upper film, which lower side surrounds each protuberance, is designed so as to be adhesive, and the blister strip comprises a lower film which covers the lower surface of the blister strip and can be pulled off from the adhesive lower side of the upper film,
wherein:
in at least one protuberance of the upper film one applicator is located, said applicator is located between first and second partial volumes of the protuberance,
the first partial volume of the protuberance is located between the applicator and the lower film,
the second partial volume of the protuberance is located between the top surface of the protuberance and the applicator and contains the medium,
each applicator has at least one opening which connects the first and the second partial volumes, and
said opening is sealed in the unopened state of the blister strip to separate said first partial volume and said second partial volume of the protuberance from each other in a sealed manner.

2. The blister strip as claimed in claim 1, wherein the upper film is a laminate consisting of a plurality of films.

3. The blister strip as claimed in claim 1, wherein the protuberance is a dome-shaped, dimensionally stable and plastically deformable dome.

4. The blister strip as claimed in, claim 1, wherein said opening is sealed by a thin membrane.

5. The blister strip as claimed in claim 1, wherein a sealing stopper closes the opening of the applicator.

6. The blister strip as claimed in claim 5, wherein the sealing stopper is adhesively bonded to the lower film, or is formed by a protuberance of the lower film.

7. The blister strip as claimed in claim 5, wherein the sealing stopper closes the entire area of the protuberance of the upper film.

8. The blister strip as claimed in claim 1, wherein the applicator is disk-shaped and is connected all the way around at the edge of the disk to the inner wall of the protuberance, wherein, in the center of the disk, the applicator has an applicator point which projects from the disk in the direction of the lower film, wherein, in the applicator point, at least one opening runs through the applicator.

9. The blister strip as claimed in claim 8, wherein the applicator point has one or more central openings, wherein, annularly around the opening, sharp or pointed elements point from the applicator point in the direction of the lower film or the skin.

10. The blister strip as claimed in claim 1, wherein the applicator has at least one pointed or sharp element which can be brought into contact with the skin.

11. The blister strip as claimed in claim 6, wherein the applicator is adhesively bonded or welded to or compressed with the upper film.

12. The blister strip as claimed in claim 6, wherein the edge of the applicator has a structured design, and the upper film is pressed in a form-fitting manner into said structure.

13. The blister strip as claimed in claim 8, wherein the edge region of the disk of the applicator is designed to be wider than the region of the disk between the edge and the applicator point.

14. The blister strip as claimed in claim 8, wherein the applicator is inserted into the protuberance in such a manner that the lower edge of the disk lies spaced apart from the adhesive lower side of the upper film.

15. The blister strip as claimed in claim 6, wherein the upper film is composed of a plastically deformable material.

16. The blister strip as claimed in claim 6, wherein the applicator is a dimensionally stable body and is formed from hard plastic.

17. The blister strip as claimed in claim 6, wherein a venting opening is present in that partial volume of the protuberance which does not contain the medium, wherein the venting opening leads into the surroundings and is closeable, or opens into a sealed expandable volume.

18. The blister strip as claimed in claim 6, wherein the medium is a liquid that contains an allergen.

19. The blister strip as claimed in claim 18, wherein the blister strip has a plurality of blisters, wherein each blister contains a medium, wherein one only contains the medium, one additionally contains histamine, and there are any desired number of blisters with distinguishable allergens.

20. The blister strip as claimed in claim 1, wherein:
the upper foil comprises multiple protuberances that are spaced to each other,
the lower side of the upper film, which lower side surrounding each protuberance, comprises an adhesive,
one applicator is inserted in each of multiple protuberances of the upper film,
in each of said multiple protuberances:
one applicator is located between two partial volumes of said protuberance,
a first partial volume of said protuberance lies between the applicator and the lower film, and
a second partial volume of said protuberance is located between the top surface of said protuberance and the applicator and contains the medium,
the applicator has at least one opening which connects two partial volumes, which opening is sealed in the unopened state of the blister strip to separate said first partial volume and said second partial volume of said protuberance from each other in a sealed manner,
at least the medium of one protuberance contains a first allergen, and
the medium of a further protuberance is selected from the group of: medium containing histamine; medium without allergen; medium that contains a second allergen.

21. A blister strip adapted to adhere to skin, comprising:
an upper film including at least one protuberance, the at least one protuberance including at least a first partial volume and a second partial volume, a lower side of the upper film surrounding the protuberance and adapted to be adhesive;
a lower film covering a lower surface of the blister strip and adapted to be detached from the lower side of the upper film; and
at least one applicator for applying onto or into the skin a medium contained in a blister of the blister strip formed by the protuberance, the medium including substances, the at least one applicator being located in the at least one protuberance of the upper film and between the first and second partial volumes, the applicator including at least one opening adapted to connect the first and the second partial volumes when the blister strip is in an opened state, the first partial volume being located between the applicator and the lower film, the second partial volume being located between a top surface of the protuberance and the applicator and containing the medium;
wherein the at least one opening is sealed in an unopened state of the blister strip to separate the first partial volume and the second partial volume from each other in a sealed manner.

* * * * *